United States Patent [19]
Bechert II

[11] Patent Number: 4,676,793
[45] Date of Patent: Jun. 30, 1987

[54] INTRAOCULAR LENS

[76] Inventor: Charles H. Bechert II, 4875 Northeast 20th Ter., Fort Lauderdale, Fla. 33308

[21] Appl. No.: 900,285

[22] Filed: Aug. 25, 1986

Related U.S. Application Data

[63] Continuation of Ser. No. 611,527, May 17, 1984, Pat. No. 4,624,670, which is a continuation-in-part of Ser. No. 483,384, Apr. 8, 1983, abandoned.

[51] Int. Cl.$^4$ .............................................. A61F 2/16
[52] U.S. Cl. ...................................................... 623/6
[58] Field of Search ........................................... 623/6

[56] References Cited

U.S. PATENT DOCUMENTS

| | | | |
|---|---|---|---|
| 4,244,060 | 1/1981 | Hoffer | 623/6 |
| 4,363,143 | 12/1982 | Callahan | 623/6 |
| 4,412,359 | 11/1983 | Myers | 623/6 |
| 4,418,431 | 12/1983 | Feaster | 623/6 |
| 4,468,820 | 9/1984 | Uhler et al. | 623/6 |
| 4,485,499 | 12/1984 | Castleman | 623/6 |
| 4,547,914 | 10/1985 | Castleman | 623/6 |

OTHER PUBLICATIONS

"Ridged Intraocular Lens May Lower Need for Discissions After Cataract Extraction", Reprint from Ophthalmology Times, vol. 6, No. 4, Apr. 1981, (2 pages).
Specifications: Model PC-11 Posterior Chamber (Advertisement), American Medical Optics, American Hospital Supply Corp., 1402 East Alton Ave., Irvine, CA 92714, Aug. 1981, 2 pages.
Specifications: Model PC-80, Posterior Chamber (Knolle), American Medical Optics, Sep. 1982, 4 pages, (Advertisement).
The Hoffer Ridge Lenses from Cilco (Advertisment Brochure) Cilco, Inc., 6 pages, Styles SK21L, S2BL, SK21LA and S2BLA, Mar. 1983.
Lens Styles from Cilco (Advertisment Brochure) 6 pages, Cilco, Inc., 1616 13th Ave., Box 1680, Huntington, West Virginia 23717, Styles SM-1, GR-1, SK-1, & SK-2.
Medical Optics PC-15L Posterior Chamber Intraocular Lens (Adverisement Brochure) American Medical Optics, Oct. 1983.
Specifications: Model PC-80, Posterior Chamber (Advertisement) American Medical Optics (1 page), Aug. 1983.
Posterior Chamber Lens, New Model 050 Posterior Chamber Lens (Brochure) 2 pages, Mar. 1983, (Intermedics, Intraocular), 623-6.
Intermedics Intraocular, Inc., Model 045 (Lester), 2 pages, (Advertisement) Intermedics Intraocular, Inc., Aug. 1982.

*Primary Examiner*—Ronald L. Frinks
*Attorney, Agent, or Firm*—Woodard, Weikart, Emhardt & Naughton

[57] ABSTRACT

An intraocular lens includes a lens body having a convex front surface and a planar back surface, an integral peripheral ring having an internal bevel extending rearwardly from the back surface, and four holes spaced about and adjacent the periphery of the lens body and extending from the front surface to the back surface. A pair of curved, filament members are attached to the lens body within apertures in bosses formed on the front surface of the lens body. Each filament member includes an inward u-niche and a distal closed loop. The u-niche makes for improved an easier insertion. The distal closed loop helps prevent iris entrapment and rupturing the posterior capsule.

4 Claims, 8 Drawing Figures

INTRAOCULAR LENS

CROSS REFERENCE

This application is a continuation of application Ser. No. 611,527 filed May 17, 1984, now U.S. Pat. No. 4,624,670, which in turn is a continuation-in-part of application Ser. No. 483,384, filed Apr. 8, 1983 and entitled "Intraocular Lens", now abandoned.

BACKGROUND OF THE INVENTION

1. Field of the Invention:

The present invention relates to the field of intraocular lenses, and more particularly to an intraocular lens for mounting within the posterior chamber of the eye.

2. Description of the Prior Art:

The lens of the human eye is situated behind the pupil and iris and functions to focus light entering through the cornea onto the retina at the rear of the eye. The lens is a biconvex, highly transparent structure made of ectodermal cells in concentric lamellae surrounded by a thin capsule. The lens capsule is supported at its periphery by suspensory ligaments, called zonules, that are continuous with the ciliary muscle. Contraction of this muscle relaxes the zonules, allowing the lens to become more spherical and thereby altering its focal length.

Under certain conditions, it is necessary to surgically remove a portion or all of the lens. For example, a cataract condition results when the material within the lens capsule becomes clouded, thereby obstructing the passage of light through the lens. To correct this condition, two forms of surgery are used. In intracapsular cataract extraction, the entire lens is removed intact by severing the zonules or suspensory ligaments about the entire periphery of the capsule. In extracapsular cataract extraction, an incision is made through the front wall or anterior capsule of the lens and the clouded cellular material within the capsule is removed. The transparent rear wall or posterior capsule remains in place in the eye, along with the zonules and peripheral portions of the anterior capsule known as the anterior capsule flaps.

Both of these procedures correct the blockage of light caused by the cataract condition. However, the light entering through the cornea and pupil is no longer focused by a lens. A variety of devices and techniques have been employed over the years to provide a substitute for the lens that has been removed or effectively destroyed by the intracapsular and extracapsular extractions. Many of these are well described in the prior art section of U.S. Pat. No. 4,244,060, issued to Hoffer on Jan. 13, 1981, and this discussion is hereby incorporated by reference.

Many of the early designs for intracapsular lenses were positioned within the anterior chamber of the eye. These devices were frequently of the type known as an iris clip lens, since the lens was clipped to the iris by pairs of projections which extended on opposite sides of the iris when the lens was in place. Examples of these anterior lenses are discussed in the Hoffer patent. Additional examples include the lenses disclosed in the following U.S. Pat. Nos. 3,673,616, issued to Federov et al. on July 4, 1972; 3,996,626, issued to Richards et al. on Dec. 14, 1976; 3,996,627, issued to Deeg et al. on Dec. 14, 1976; 3,925,825, issued to Reykers on Dec. 16, 1975; and, 4,079,470, issued to Deeg et al. on Mar. 21, 1978. A related type of lens is disclosed in U.S. Pat. No. 4,014,049, issued to Richards et al. on Mar. 29 1977, which lens is mounted in the posterior chamber but is secured to the iris.

The prior art also discloses a variety of intraocular lenses which are designed for mounting within the posterior chamber. There is disclosed in the Hoffer patent, for example, a lens which is stated to be particularly adapted for implantation in the posterior chamber after extracapsular cataract extraction. The Hoffer lens includes several lens-centering filaments which extend outwardly in a common plane from the rim of the lens body. These filaments are inserted within the cleft of the capsule to secure the lens within the eye and to center the lens behind the pupil.

The Hoffer lens also includes an annular lip which projects from the rear face of the lens body and is intended to seat against the posterior capsule. At least one opening in the annular lip is provided to permit the insertion of a discission instrument therethrough and into the space behind the lens. The Hoffer patent further notes that the lip limits the progress of vitreous humor toward the anterior chamber after a discission, and may limit lens fiber growth on the posterior capsule within the lip region.

A related intraocular lens is now shown in promotional literature of CILCO, Inc. of Huntington, West Virginia and is said to be available under the designation "HOFFER RIDGE LENS." This lens includes a body portion which has a convex front surface and a planar rear surface. An annular ridge extends rearwardly from and perpendicular to the rear surface adjacent the periphery of the lens. Instead of having several fine filaments as in the patent, the HOFFER RIDGE LENS includes only a pair of curved filaments, probably of greater thickness than those contemplated in the patent, and which extend outwardly from the lens body at diametrically opposed locations. Each filament extends nearly tangentially from the lens body and, in one version they curve in a "J" configuration, with the bottom of the "J" being positioned for seating the lens within the posterior chamber. Another version uses a "C" configuration.

In U.S. Pat. No. 4,110,848, issued to Jensen on Sept. 5, 1978, there is also disclosed an intraocular lens for implantation into the posterior chamber of the eye. The Jensen lens includes a pair of loops which extend outwardly from opposite sides of the lens body at a slight rearward angle. One of the loops includes a notch disposed between its end portion and the peripheral edge of the lens body so that a temporary securement to the iris of the eye may be accomplished.

Another posterior chamber lens is available from Intermedics Intraocular Inc. of Pasadena, California under the designation "LESTER POSTERIOR CHAMBER INTRAOCULAR LENS." The LESTER INTRAOCULAR LENS includes a lower or inferior closed loop which extends from the lens body and also an upper or superior J-shaped filament extending from the lens body. The superior filament includes a positioning notch located slightly inward of the base of the "J" shaped filament and opposite the free end of the filament. The LESTER INTRAOCULAR LENS also includes a single, small positioning hole slightly inward of the top edge of the lens body.

Currently available are two lenses which include outwardly extending filaments which have closed loops on the ends of the filaments. One such lens is known as the "PANNU LENS" and is marketed by American Medical Optics. A second lens having the closed loop at the end of a mounting filament is available from IOLAB under the designation "OSHER LENS." Neither of these lenses includes a centering notch on the filament. There is a Knolle PC-80 lens which has two filaments, one at the top and one at the bottom, with a depression or notch in one side of each filament loop.

Various other devices and techniques have been developed in conjunction with intraocular lenses intended for mounting within the posterior chamber. Lenses including other configurations for the mounting projections of the lens are disclosed in U.S. Pat. Nos. 4,251,887, issued to Anis on Feb. 24, 1981; 4,092,743, issued to Kelman on June 6, 1978; and 3,906,551, issued to Otter on Sept. 23, 1975. A method for implanting an intraocular lens is described in U.S. Pat. No. 4,159,546, issued to Shearing on July 3, 1979.

SUMMARY OF THE INVENTION

Briefly describing one aspect of the present invention there is provided an intraocular lens for mounting within the posterior chamber which comprises a lens body having a convex front surface and a planar back surface, the lens body including an integral ring extending rearwardly from the back surface. The lens also has a plurality of holes adjacent the ring. Resilient filament members are attached to and extend from the lens body at diametrically opposed positions. Each of the filament members includes an inward niche and terminates in a closed loop.

It is an object of the present invention to provide an intraocular lens adapted for implantation within the posterior chamber.

Another object of the present invention is to provide an intraocular lens which is readily implanted within the posterior chamber, and particularly which includes a variety of design features to facilitate handling, implantation and adjustment of the lens.

It is a further object of the present invention to provide an intraocular lens which is constructed to fit correctly within the posterior chamber and provide a relatively large area of the rear of the lens free of contact with the posterior capsule.

Another object of the present invention is to provide an intraocular lens which facilitates the further treatment of the eye either by ready removal of the lens or by procedures performed with the lens remaining within the eye, such as light frequency or laser capsulotomy, for example.

Further objects and advantages of the present invention will become apparent from the description of the preferred embodiment which follows.

DESCRIPTION OF THE PREFERRED EMBODIMENT

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring in particular to the drawings there is shown an intraocular lens 10 constructed in accordance with the preferred embodiment of the present invention. The lens 10 is particularly adapted for implantation within the posterior chamber of the eye. The lens includes a pair of resilient filament members 11 and 12 which are attached to and extend outwardly from a lens body 13.

Figure 1:
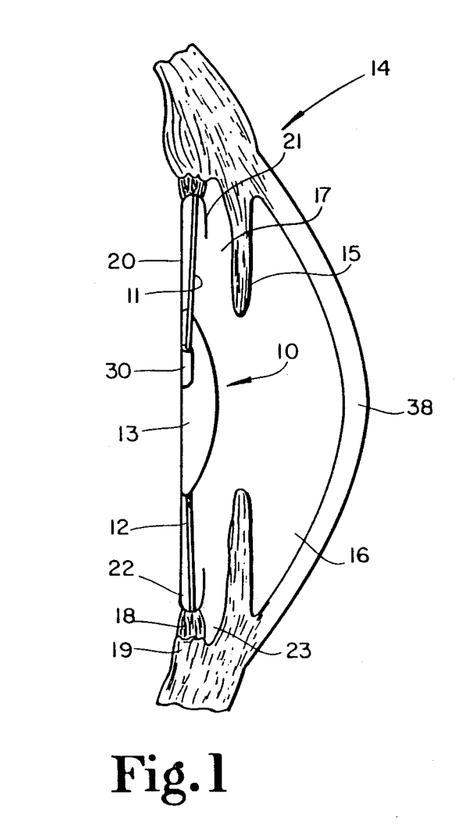
FIG. 1 is a side, sectional view showing an intraocular lens according to the present invention implanted within the posterior chamber of an eye.

A human eye 14 includes an iris 15 which separates the interior into an anterior chamber 16 and a posterior chamber 17. The lens of the eye is supported within the posterior chamber by the suspensory ligaments or zonules 18 extending from the ciliary muscle in the eye wall region 19. Upon extracapsular extraction of the lens, there remains intact the posterior capsule 20 of the lens, along with an annular flap portion 21 of the anterior capsule. As shown in FIG. 1, the intraocular lens 10 is preferably implanted within the capsular bag 22 between the posterior capsule 20 and the flap 21. Alternatively, the lens may be implanted with the filament members received within the ciliary sulcus 23.

The intraocular lens has a generally disc-shaped lens body 13 including a convex front surface 24 and a planar back surface 25. The lens body may be provided in a variety of dioptric powers, typically ranging from 10 to 26. The diameter of the lens body may vary as required, and preferably is about 7.0 mm. The use of 7 mm. optics and interior bevel to be described reduces the possibility of glare and distortion of vision as compared to smaller diameter lenses.

Figure 4:
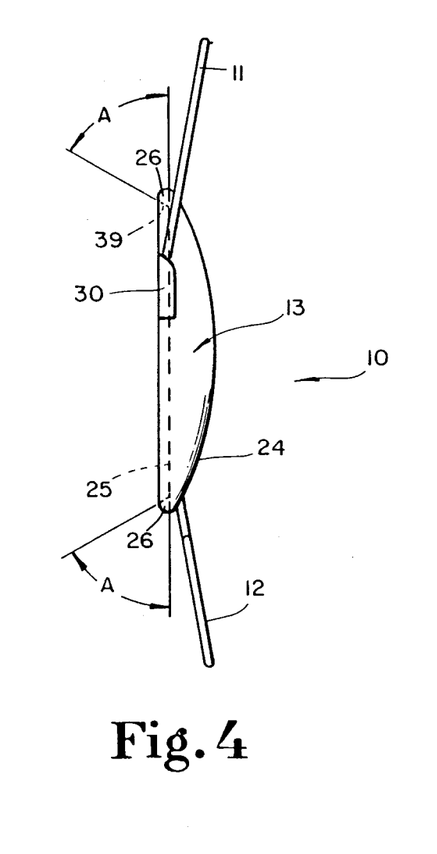
FIG. 4 is a side, elevational view of the lens of FIG. 2.

The lens body 13 has an integral ring 26 extending rearwardly from the back surface 25. The ring 26 preferably forms a closed circle having a preferred diameter of about 7.0 mm. The ring has a preferred thickness or width from side-to-side of about 0.50 mm. The ring is generally circular in cross section as shown in FIG. 4. It is positionable against the posterior capsule 20, as shown particularly in FIG. 1. and thereby spaces the back surfaces 25 of the lens away from the posterior capsule a distance substantially equal to the height of the ring, i.e. 0.25 mm. where the height of the ring is 0.25 mm.

The presence of this ring displacing the lens anteriorly, and providing a space between the planar back surface 25 of the lens body and the posterior capsule, permits improved efficiency of posterior capsulotomy procedures by laser technique. The YAG Laser, for example, may be readily used in conjunction with the intraocular lens of the present invention with the lens remaining in place during the posterior capsulotomy. The spacing of the back surface of the lens body from the posterior capsule reduces the possibility of pitting, cracking or fracturing of the lens which could otherwise occur if the laser is not precisely focused on the posterior capsule.

The lens body further includes four holes, such as 27 and 28, located proximate to the ring and substantially equally spaced about the portion immediately radially inward from the ring. The holes extend from the front surface 24 to the back surface 25, and are provided to facilitate positioning and rotation of the lens after implantation within the eye. Placement of the holes substantially at the four, cardinal positions shown in the drawings provides maximum convenience for use of the holes in positioning the lens. The holes preferably have a diameter of less than about 0.25 mm., with this small size being desirable to reduce the possibility of glare which may otherwise be produced.

Figure 3:
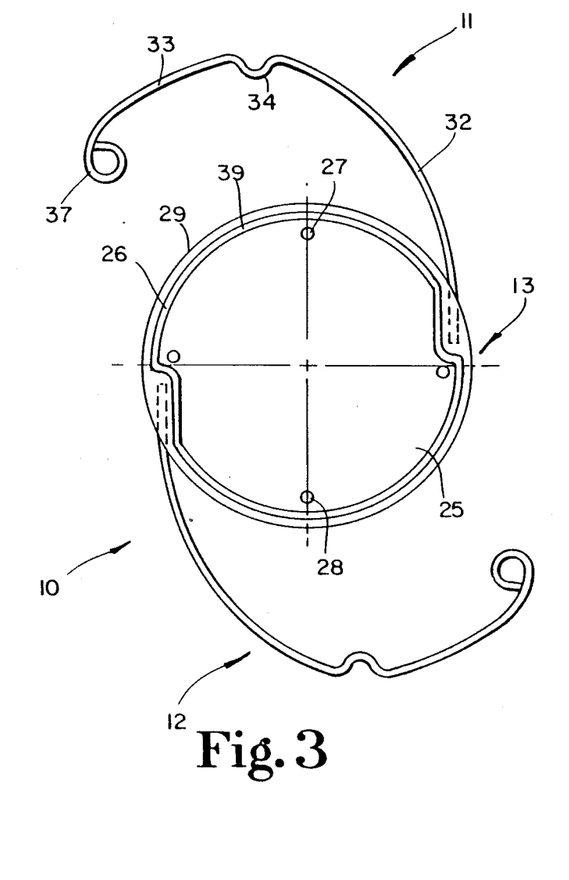
FIG. 3 is a rear, elevational view of the lens of FIG. 2.

According to another feature, an internal bevel as at 39 (FIGS. 3 and 4) is provided on the ring from the rear lens face 25 out to a location near the plane of the rearward surface of the ring. It blends into the rest of the generally circular cross sectional shape of the ring immediately ahead of this plane. This bevel may be at an angle "A" of 60 to 85 degrees from the plane of the lens face 25.

The lens 10 also includes a pair of resilient filament members 11 and 12. Such members associated with intraocular lenses are sometimes called "haptics". The lens body 13 includes a pair of front bosses 30 and 31 which are located forwardly of the back surface of the lens body, and which extend outwardly of the front surface. Each front boss includes an aperture within which the proximal end of one of the filament members is received and secured. Use of the bosses on the front surface enables the lens body to have a reduced thickness and weight. The filament members extend from the bosses at a forward angle of about 10° to the plane of the back surface (FIG. 4). The invention is not limited to this angle, as it will work even if the filaments are parallel to the plane of the back surface. Rear bosses can be seen in FIG. 3. These cooperate with the front bosses to accommodate the proximal ends of the filaments. The above-mentioned bevel is continued on these rear bosses.

Each of the filament members is formed identically with the other in the following configuration. The filament members project from the lens body in a curve having a first part 32 and a second part 33. In the free, unstressed condition of the filament members, the first part 32 of the curved filament member extends at a progressively increasing radially distance from the center of the lens body. The second part 33 of the curved filament member extends generally concentrically with the lens body at a substantially constant radius.

Each filament member further includes a niche, such as 34, which is useful during insertion of the lens into the posterior chamber. The niche 34 is located along the filament member other than within the first part of the curve, and preferably is located at about the junction of the first and second parts of the curve.

Figure 2:
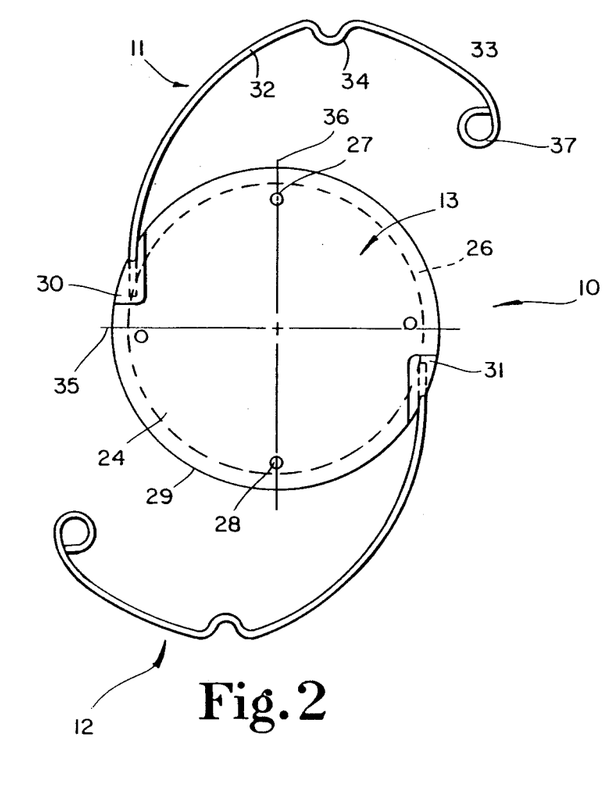
FIG. 2 is a front, elevational view of an intraocular lens constructed in accordance with one embodiment of the present invention.

In particular, the niche is preferably located at a position at or slightly more than about 90° from the radial line, such as 35, which extends perpendicular to the direction of the proximal end of the filament member. Correspondingly, the first part of the curved filament member extends about the lens body at least about 90°. For example in FIG. 2, the proximal end of filament member 11 extends vertically in the drawing and the radial line 35 extends horizontally, or perpendicular to the proximal end. The vertical, or meridian radial line 36 is 90° from the line 35 and the niche 34 is positioned on or slightly to the right of the line 36. This positioning of the niche is more anatomically correct in use of the intraocular lens. Heretofore, notches have been used which are located in the lateral surface of the filament. According to my invention, the niches, being U-shaped and located at the juncture of the two bends in filament and placed on or adjacent the meridian of the lens, makes compression of the filament more uniform and facilitates the insertion of the implant without the possible slippage of the inserting instrument. This placement of the niche provides for a more stable manipulation of the lens unit during insertion in the eye.

The distal end of each of the filament members is spaced apart from the lens body, and forms a closed loop, such as 37. These closed loops are particularly beneficial in several respects. First, they prevent catching of the iris or perforation of the posterior capsule by the filament. Also they aid in uniplanar positioning of the lens in the posterior capsule. That is, it is desirable that both filaments are situated in the posterior capsule, rather than having one remain in the ciliary sulcus. While it is most desirable that both be in the capsule, it would be better to have both in the ciliary sulcus than one there and one in the capsule. Otherwise tilting or "torque" of the lens can result, and that is undesirable. The filament members of this embodiment preferably extend over to at least as far as about the edge of the lens body opposite the location of attachment of the filament member to the lens body. For example, in FIG. 2 the filament member 11 is attached to the lens body 13 at the left edge, and the filament member extends to the right beyond the right edge of the lens body.

The filament members extend outwardly of the lens body to have an overall span somewhat greater than the space within which the lens is to be implanted. The filament members are formed of a resilient material, suitable for implantation, which permits the members to be flexed inwardly to facilitate insertion into the posterior chamber. This resiliency also results in the filament members expanding outwardly within the posterior chamber to seat within and bear against the capsular bag or ciliary sulcus. The filament members thereby secure the lens within the posterior chamber in the desired position. The filament members may have a variety of overall spans to accommodate various sizes and shapes of eyes, and typically would have a span of about 14.25 mm. The substantial span decreases the possibility of the lens decentering or moving in larger eyes. The relatively large diameter and therefore optical zone of the lens body, preferably about 7.0 mm. in diameter, also operates to minimize optical effects resulting from decentration.

As described, the intraocular lens of the present invention is conveniently configured to facilitate its handling, implantation, and adjustment, as well as fitting properly within the posterior chamber. The niches and loops are located in proper position to permit a correct, convenient and stable positioning of the filament members. The identical configuration and opposed placement of the pair of filament members, including particularly the positioning of the niches and closed distal loops, ensures a balanced design for the lens.

The intraocular lens 10 of the present invention is implanted into the posterior chamber in accordance with the following general technique. An incision is made around a portion of the periphery of the cornea 38 and the pupil is dilated. The iris is depressed slightly to permit the lower filament member to be inserted, preferably into the capsular bag, or alternatively into the ciliary sulcus. The other filament member is then guided into position opposite the first filament member and the lens is rotated or otherwise adjusted to the final, desired position. In performing these steps, any suitable combination of the niches, distal closed loops or adjusting holes provided for the lens may be used to facilitate manipulation of the lens into and within the eye. Upon final positioning of the lens within the posterior chamber, the resilient filament members will properly hold the lens body in a centered location posterior to the iris.

The components of the lens body and filament members may be formed from a variety of materials suitable for implantation, and which provide the necessary physical characteristics to the component. Various clear plastics, such as polymethyl methacrylate, are known to be useful for formation of a lens body of the type used in the present invention. The filament members may similarly be formed from materials and in cross-sectional thicknesses known to be useful in this type of application including, for example, polypropylene. It is now possible to make an entire unit, including not only the lens body but also the filaments, as a single homogeneous unit of polymethyl methacrylate, and still do the flexing of the filaments as needed during implantation procedure, without cracking the filaments. An example of this is present in the preferred embodiment shown in FIGS. 5 through 8 herein where all of the above-mentioned bosses are eliminated.

Figure 5:
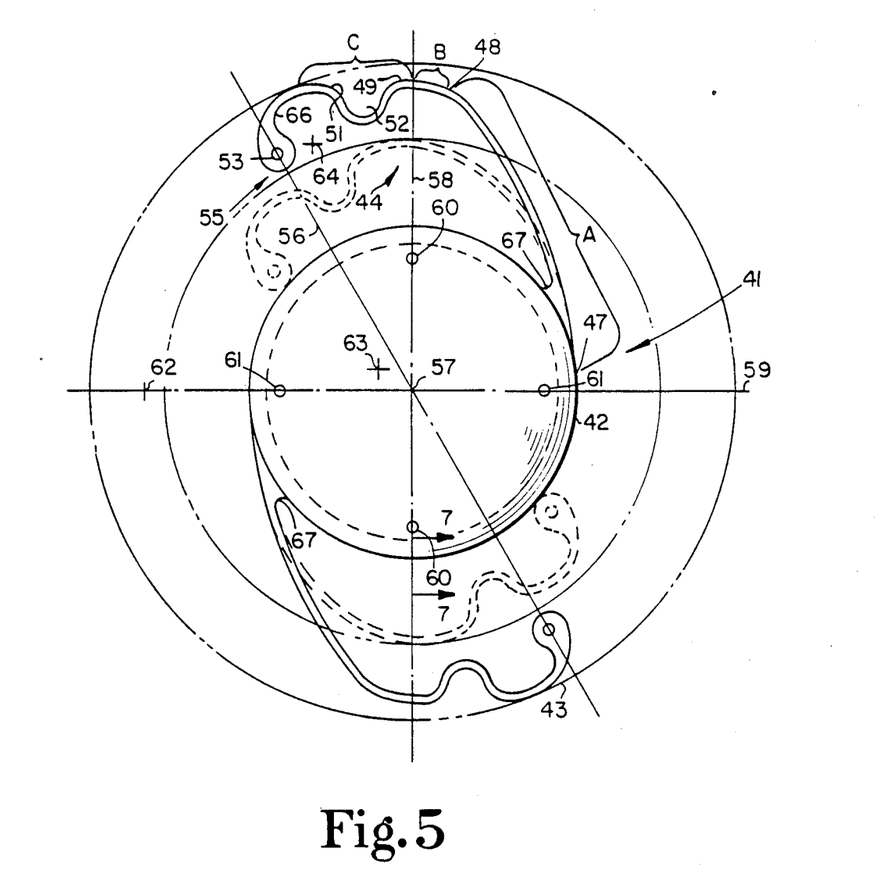
FIG. 5 is a front elevational view showing a second and preferred embodiment of the present invention.

Referring now to FIG. 5, the lens 41 has the two filaments (haptics) shown by solid lines in the unstressed, relaxed condition. It has a seven millimeter diameter optic portion to the outer marginal edge 42. In the free, unstressed state, the filaments extend to an outer circle 43 of 14 millimeters diameter. The filaments are of one integral homogeneous mass of material with the optic and extend from two diametrically opposed locations on the lens.

Filament 44 includes what may be referred to as a first portion "A" which begins tangent the optic at 47 and continues to a "knee" 48. A second portion "B" extends from the knee 48 to a knee 19. A third portion "C" extending from knee 49 through knee 51 includes the niche 52. The fourth portion extends from the end of the third portion tangent circle 43 to the end loop 55 having a central aperture 53 located approximately 2.40 millimeters from the peripheral edge 42 of the optic.

Since most eye surgeons are right-handed, and it is desirable to slightly rotate the lens following placement of the filaments in the capsular bag 22, the filaments in this lens are generally curved in a counterclockwise direction (viewed from the front of the lens) as they extend outward from the lens. They have a diameter of about 0.15 millimeters, except at the end loops which are 0.15 millimeter thick but have a 0.375 millimeter radius about the axis of apertures 53. The combination of the third portion "c" of the filament and that part of the fourth portion extending from the third portion to a radius 56 from the lens axis 57 to the axis of the loop aperture 53, subtends an angle of 30° with respect to the radial line 58.

Figure 6:
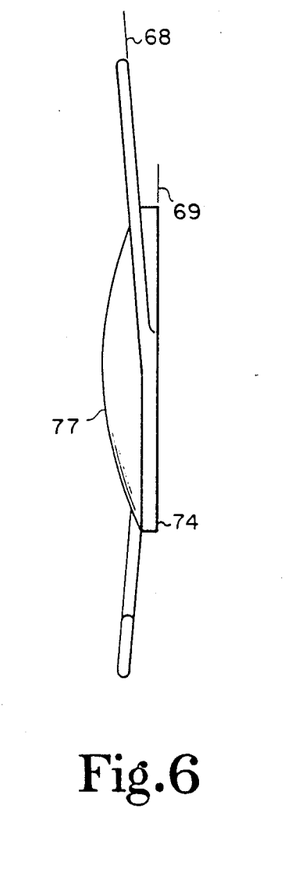
FIG. 6 is a side elevational view of the preferred embodiment.
Figure 7:
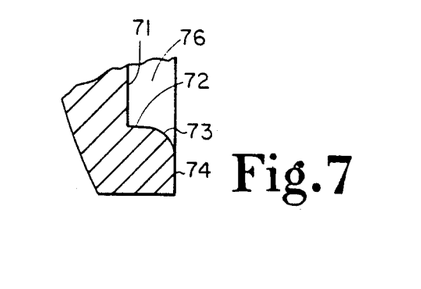
FIG. 7 is an enlarged sectional view taken at line 7—7 in FIG. 5 and viewed in the direction of the arrows.

The first portion of the filament is arcuate about a center at 62 on a line 59 extending through two of the four positioning apertures 61 and the lens axis, and has a radius of between 9.30 and 9.50 millimeters. The second portion "B", is also arcuate, having a center at point 63 located 0.47 millimeters up from line 59 and 0.75 millimeters to the left of line 58. It has a radius of between 6.15 and 6.35 millimeters. Both the knees 49 and 51 at the ends of the third portion are tangent a circle about center 63 defining the arc of the second portion "B". The radius of the arc of the fourth portion is 1.10 to 1.30 millimeters and centered at point 64. The radius of the niche 52 is preferably 0.30 to 0.50 millimeters. This is the preferable radius also at the inside of the knees 49 and 51 and at the location 66. The loop apertures 53 are of the same 0.25 millimeter diameter as are the positioning apertures 60 and 61. They are located between 2.25 and 2.55 millimeters from the peripheral edge 42. The radius of the fillet inside the junction of the filament with the optic at 67 is typically 0.20 millimeters. As best shown in FIG. 6, each filament is planar and extends outward from the optic in a plane such as plane 68 at an angle of 10° from the plane 69 of the back surface of the ring.

The ring projects to the rear from the flat back surface 71 of the optic and is uniform and homogeneous around its circumference. It has an inner wall 72 with a draft of 3° and a radius blend at 73 between this wall and the back surface 74 of the ring. The diameter of wall 72, and thereby the optic, is preferably between 6.10 and 6.30 millimeters, as great as possible consistent with a reasonable area of ring back surface and blend at 73 to avoid light reflections at the edge. The depth of the cavity 76 from the plane 69 to the optic back surface 71 is 0.20 to 0.25 millimeters. The resulting 0.20 to 0.25 ring height facilitates use of the YAG laser, without damage to the lens, as discussed above. This height, together with the continuity and shape of the ring, has the expected effect of decreasing the migration of germinal cells to the optical zone of the posterior capsule, thus reducing capsular opacification. The radius of the convex face 77 of the lens depends upon the lens power needed for the visual performance to be achieved with the lens.

Figure 8:
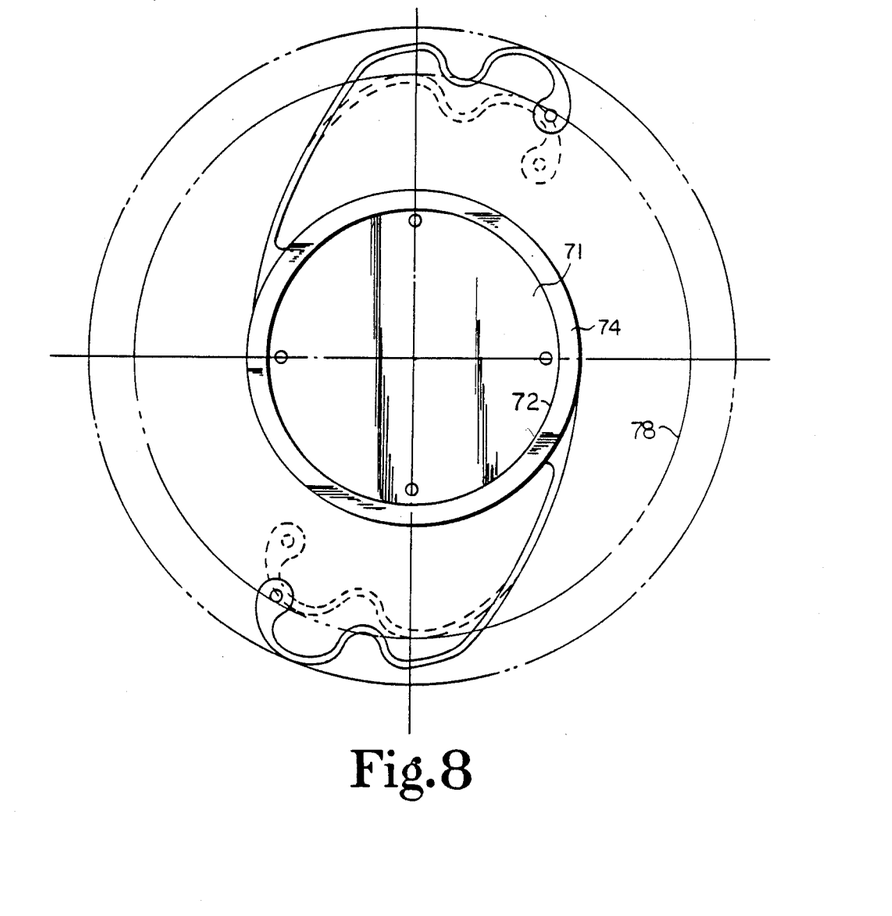
FIG. 8 is a rear view of the preferred embodiment.

If the lens of this embodiment is placed in the ciliary sulcus of the eye as at 23 in FIG. 1, instead of within the capsular bag 22, it will have an appearance much as shown in the unstressed state shown in the solid lines in FIG. 5. The diameter of circle 43 is approximately 14 millimeters. If the lens is placed in the capsular bag 22, the filaments may be confined within a circle which can vary from 11 millimeter to 12 millimeter diameter. The dotted outline in FIG. 5 shows the attitude of these filaments when they are confined within a circle of 11 millimeter diameter. In this instance, instead of the third and fourth portions of the filaments being the outermost, it is the second portion which is at the maximum diameter when the filaments are thus resiliently stressed in this confinement, and these are tangent the inner wall of the ciliary sulcus. In both attitudes of the "A" filament portion, that shown by the solid line in FIG. 5 and that shown by the dotted line, a portion of the filament is proximate the confinement tissue. At the 14 millimeter diameter, it is the third-fourth portion. In the 11 millimeter confinement, it is the second portion. At the same time, the adjacent portion is very close to the peripheral confining tissue. In this manner, regardless of the cavity in which the lens is deposited, within the above-mentioned 11 to 14 millimeter limits, these filaments provide something that simulates a four-point fixation in the eye. This is different from other lens configurations of which I am aware, in that it gives more stability and less torquing in the eye. It also gives less contact with the ocular structures but, at the same time, affords good stability. To avoid clutter in FIG. 5, dotted lines are included in the rear view of FIG. 8 to show the more typical attitude of the filaments when the circle of the confinement tissue represented at circle 78 in FIG. 8 is about 12 millimeters in diameter. This is the ideal situation and, due to the resilience of the filaments and some compliance of the tissue, the four point contact with tissue as at circle 78 is achieved in many cases.

The holes 53 facilitate maneuvering the lens. The same is true of the holes 60 and 61. The niches at 52 facilitate insertion of the lens into the superior capsule or bag. The ring provides the desired 0.25 millimeter separation between the lens and posterior capsule after insertion into the eye and thus facilitate laser capsulotomy if necessary at some later time. Meanwhile, because of the expected effect of the continuous ring in reduction of migration of cells across the posterior capsule, opacification of the capsule should be reduced and the necessity for capsulotomy postponed or avoided. The lens is very flexible, having a somewhat linear force/compression characteristic such as 0.13 grams for 0.5 millimeter, 0.3 grams for one millimeter, and a maximum force of approximately one gram to achieve a three millimeter compression distance.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. The terminology "front" and "back" and "forward" as used in claims hereinafter, is intended to establish relationships in the lens itself, but not be construed as limitations with respect to whether it is "front" or "back" when in the eye in which it is to be used.

The invention claimed is:

1. An intraocular lens for implantation within the eye, said lens comprising:
    a lens body having a central axis and a back surface and a convex front surface; and
    a pair of resilient filament members extending outwardly from said lens body at substantially diametrically opposed positions, each of said filament members having a proximal end at said lens body and a distal end spaced apart from said lens body, at least one of said filament members including an inward niche having a depth greater than the thickness of the filament member and located intermediate the proximal and distal ends, each of said filament members projecting from said lens body in curves having a first part and a second part, the first part extending at a progressively increasing radial distance from said axis of said lens body, the second part extending generally concentrically with said lens body, the filament members being shaped and the niche located to provide at least three point fixation of the lens in the confinement tissue of the eye.

2. The lens of claim 1 in which the niche is located outboard of the first part of the curves and at a distance from the lens body such that, when the filament members are confined within any confinement circle centered on said axis and having a diameter between 11 and 13 mm., the filament members are resiliently deformed and each filament member is resiliently urged outward into contact with the confinement circle, said at least one filament member being urged into contact with the confinement circle at a first point on at least one side of the niche while a second point on the opposite side of the niche is less than the said niche depth away from said confinement circle, to thereby provide at least three point fixation of the lens in the eye when the filament members resiliently engage tissue in the eye.

3. The lens of claim 2 in which the said at least one filament member includes the niche located at the junction of the first and second parts of the curves of said filament member.

4. An intraocular lens for implantation within the eye, said lens comprising:
    a lens body having an axis, a back surface and a front surface, said front surface being convex;
    a pair of resilient filament members extending from said lens body to substantially diametrically opposed locations, each of said filament members being resiliently deformable from a free, relaxed configuration and condition, to a contracted condition to facilitate insertion into a chamber of an eye adjacent the pupil, each filament member in the free, relaxed configuration having a first portion extending outward from a perimetrical location on the lens body, and a second portion having an arc extending circumferentially about a center adjacent the lens axis, at least one of said filament members having third, fourth and fifth portions in sequence from said second portion, said third portion being an inward niche, said fourth portion having a radius substantially less than the radius of said arc, and said fifth portion being a distal end portion with a loop at the distal end, whereby the filament members are adapted to resiliently engage confinement tissue in the eye at least at three points, said points being at the second and fourth portions of said one filament member on opposite sides of the niche to establish at least three-point fixation of the lens in the eye.

* * * * *